United States Patent
Shapiro et al.

(10) Patent No.: US 6,254,859 B1
(45) Date of Patent: Jul. 3, 2001

(54) HAIR AND SKIN CONDITIONING COMPOSITIONS

(75) Inventors: Irene Shapiro, Buffalo Grove; Galina Tseitlina, Deerfield, both of IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 09/369,474

(22) Filed: Aug. 6, 1999

Related U.S. Application Data

(63) Continuation of application No. 09/003,295, filed on Jan. 6, 1997, now abandoned, which is a continuation of application No. 08/529,306, filed on Sep. 18, 1995, now Pat. No. 5,705,147.

(51) Int. Cl.⁷ ..................................................... A61K 7/075
(52) U.S. Cl. .................. 424/70.1; 424/70.13; 424/70.22; 424/401; 424/70.19
(58) Field of Search ............................... 424/70.1, 70.13, 424/70.22, 401, 70.19

(56) References Cited

U.S. PATENT DOCUMENTS

| 4,210,161 |   | 7/1980 | Wagman . |
| 4,377,685 | * | 3/1983 | Bouniot et al. ................... 536/119 |
| 4,902,499 |   | 2/1990 | Bolish, Jr. et al. . |
| 5,705,147 | * | 1/1998 | Shapiro et al. .................. 424/70.1 |

FOREIGN PATENT DOCUMENTS

| 0 335 404 | 10/1989 | (EP) . |
| 0 370 764 | 5/1990 | (EP) . |

* cited by examiner

*Primary Examiner*—Raj Bawa
(74) *Attorney, Agent, or Firm*—McDonnell Boehnen Hulbert & Berghoff

(57) ABSTRACT

Disclosed are compositions for cleaning and conditioning of hair and/or skin comprising a mixture preparable by transesterification of a triglyceride with sucrose. These compositions typically further comprise various surfactants and optional ingredients depending on the specific composition desired.

21 Claims, No Drawings

HAIR AND SKIN CONDITIONING COMPOSITIONS

This is a continuation of U.S. application Ser. No. 09/003,295, filed Jan. 6, 1997, now abandoned, which is a continuation of U.S. application Ser. No. 08/529,306, filed Sep. 18, 1995, now U.S. Pat. No. 5,705,147.

BACKGROUND OF THE INVENTION

1. Field of the Invention

The present invention relates to conditioning compositions for skin and hair. More specifically, it relates to skin and hair conditioning compositions containing sucroglyceride conditioning agents, hair conditioners and hair conditioning shampoos.

2. Description of the Related Art

Human hair becomes soiled due to its contact with the surrounding atmosphere and, to a greater extent, from sebum secreted by the head. The build-up of sebum causes the hair to have a dirty feel and an unattractive appearance. The soiling of the hair necessitates it being shampooed with frequent regularity.

Shampooing the hair cleans by removing excess soil and sebum. However, the shampooing process had disadvantages in that the hair can be left in a wet, tangled and generally unmanageably state. Shampooing can also result in the hair becoming dry or "frizzy" due to the removal of natural oils or other hair moisturizing materials. After shampooing, the hair can also suffer from a perceived loss of "softness". Softness, of course, is a generally desirable attribute for many users of shampoo products. A variety of approaches have been developed to alleviate the after-shampoo problems. These range from the use of after-shampoo conditioning treatment, i.e., hair-rinses, to the inclusion of hair conditioners into the shampoo compositions themselves, i.e., conditioning shampoos.

Hair rinses typically work by depositing a polymeric film, cationic hair conditioning surfactant, or other material onto the hair. However, such compositions, due to a variety of problems, have not been fully satisfactory. For example, hair rinses are generally liquid in nature and must be applied in a separate step following the shampooing, left on the hair for a length of time, and rinsed with fresh water. This, of course, is time consuming and is not inconvenient.

Conditioning shampoos containing cationic conditioning agents have been disclosed in, for example, EP 018 717. These cationic agents confer some conditioning benefit on hair, but are often thought to leave a residue on the hair, which may cause dulling of hair after drying.

Non-volatile silicone oils are useful as conditioning agents. However, the use of such oils is associated with some difficulties. A particularly difficult problem encountered with shampoos containing such oils is maintaining the insoluble silicone oil stably suspended. A variety of materials have been proposed for use in silicone-containing shampoos to thicken and stabilize the shampoo. These materials include, for example, xanthan gum, long chain acyl derivatives, long chain amine oxides, and long chain alkanolamides. These materials are disclosed in U.S. Pat. Nos. 4,788,006, 4,704,272, and 4,741,885. In addition, excessive amounts of silicone can dull hair, and buildup of silicone on the hair can give a greasy appearance. Furthermore, incorporation of silicone oils generally yields a foam suppressing effect. Accordingly, there exists a need for conditioning agents capable of overcoming these problems.

SUMMARY OF THE INVENTION

The present invention provides cleaning and conditioning formulations for human skin and hair comprising a sucroglyceride composition in a base formulation. Thus, the invention encompasses conditioning shampoos and various personal care formulations. Representative compositions include, for example, facial cleansers, bubble bath and gel, bar and liquid soaps, shaving creams, and antidandruff shampoos. It further encompasses other cleaning compositions containing a surfactant or detergent base. Representative of these other cleaning compositions are light duty dishwashing liquids.

The invention also provides methods for conditioning human hair or skin comprising contacting human hair or skin with an effective conditioning amount of a sucroglyceride composition.

The sucroglyceride compositions suitable for use in the invention are anionic in character, i.e., they include an anionic component together with noionic components. The sucroglycerides of the invention typically comprise sucrose monoesters, slats of the aliphatic fatty acids derived from the triglyceride (soaps), sucrose, monoglycerides, glycerin, and a mixture of diglycerides and triglycerides.

The inventive compositions enjoy a variety of advantages over known conditioning agents. Sucroglycerides are derived from natural sources, non-toxic, and readily biodegradable. In addition, they are odorless, tasteless and mild to human skin. Sucroglycerides are non-sensitizing; they are non-allergenic and do not cause skin irritation. Further, sucroglycerides function as excellent emulsifiers for a wide range of oils. In addition, they are self-emulsifying and self-suspending. Further, the can be easily combined with conventional anionic, cationic, and nonionic surfactants to provide many different conditioning formulations. Further, sucroglycerides do not suppress foam produced by surfactants and do not cause build-up on hair. The sucroglycerides also provide a temporary pearlescent effect to shampoos and other detergent based personal care compositions.

The sucroglycerides of invention comprise a mixture of products resulting from the reaction between sucrose and a triglyceride. The sucroglycerides of the invention may optionally be prepared by mixing the required amount of each of the components required to achieve a specific sucroglyceride composition.

DETAILED DESCRIPTION OF THE INVENTION

Unless otherwise indicated, the amounts of all components described herein are indicated in percent by weight.

As used herein, the term "sucroglyceride" or "sucrose glyceride" means a mixture of products (1) obtained directly from the transesterification between sucrose and natural or synthetic triglycerides; this mixture contains monoglycerides. diglycerides, unaltered triglycerides, sucrose esters and soaps; or (2) obtained by combining predetermined amounts of sucrose, sucrose esters, glycerin, monoglyceride, di- and triglycerides, and soap (salts of fatty acids).

As used herein, "triglyceride" means one or more triglyceride(s) of saturated or unsaturated aliphatic fatty acids having at least 8 carbon atoms, preferably 8–22 carbon atoms, and more preferably from 8 to 18 carbon atoms. Although synthetic triglycerides can be obtained from a reaction of glycerol and fatty acid, it is preferable to use naturally occurring triglycerides, i.e., mixtures of triglycerides.

By "build-up", as used herein, is meant a greasy or oily feel and/or appearance on hair caused by deposition on hair of successive layers of conditioning agents, such as cationic polymers, cationic surfactants, silicone oils or combinations of thereof.

Representative naturally occurring triglycerides include, for example, lard, tallow, peanut oil, butter oil, cottonseed oil, linseed oil, coconut oil, olive oil, palm oil, grapeseed oil, fish oil, soybean oil, castor oil, copra oil, rapeseed oil, tall oil, sunflower oil, sorghum oil, sesame oil, safflower oil, palm kernel oil, linseed oil, and corn oil.

Preferred sucroglycerides for use in the invention include sucroglycerides derived form cottonseed oil, palm oil, and tallows. The sucroglycerides suitable for use in the invention are predominately nonionic and include an anionic component in addition to the nonionic components. The anionic component is typically soap or soaps, i.e., salts of the fatty acids derived from the triglyceride. Preferred sucroglycerides for use in the invention are those capable fo providing a conditioning effect to human hair or skin (the substrate) when allowed to contact the substrate. When such sucroglycerides contact the substrate, they are deposited on the substrate whereby they provide a "conditioned feel" to the substrate. This conditioned feed is apparent, for example, during wet and dry combing of human hair. It is also observed as a smooth or silky after-feel on skin or hair.

The sucroglycerides of the invention typically are in the state of a solid, semi-solid, or paste depending on the composition and triglyceride chain length. Thus, they may be low melting solids having melting points of from about 75 to 80° C. These sucroglycerides may be prepared by a transesterification reaction between a triglyceride and sucrose. The reaction is conducted in the presence of at least a catalytic amount of a strong base, preferably an alkali metal salt. The reaction is mixed at a high degree of shear at a temperature of about 125° C. and allowed to proceed for about 7 to 15, preferably 10, hours. Alternatively, as noted above, the sucroglyceride may be prepared by combining predetermined amounts of sucrose, sucrose esters, glycerin, monoglyceride, di- and triglycerides, and soap (salts of fatty acids).

Sucroglycerides suitable for use in the invention contain, by weight percent, form about 1–40% of sucrose monoesters, about 5 . 50% of salts of the aliphatic fatty acids derived from the triglyceride (soaps). about 0–30% of sucrose, about 5–40% monoglycerides, about 0.5–25% by weight of glycerin, and about 1–55% of diglycerides and triglycerides. The sucroglycerides may optionally comprise sucropolyesters.

Preferred sucroglyceride compositions consist essentially of about 2–30% by weight of sucrose monoesters, about 10–40% by weight of salts of the aliphatic fatty acids derived from the triglyceride, about 0–20% by weight of sucrose, about 2–35% by weight monoglycerides, about 0.5–20% by weight of glycerin, and 2–55% by weight of a mixture of diglycerides and triglycerides.

The sucroglyceride is typically present in the conditioning formulation in an amount sufficient to impart a satisfactory feel to the substrate, i.e., an amount effective for conditioning. Preferred amounts are from about 0.5 to 15% by weight of the formulation. More preferably a formulation, e.g., a conditioning shampoo, will comprise about 2–10%, and most preferably from about 3–7% by weight, of the sucroglyceride.

The conditioning formulations and cleaning compositions typically include various base components and optional components. Where the formulation is intended for use as a cleaning formulation, e.g., a hair shampoo, bath gel, or dishwashing liquid, the base component(s) will be a surfactant(s) acting as a detergent(s).

Hair conditioning formulations according to the invention optionally include one or more carriers, typically including water. The shampoo compositions hereof are typically characterized by the presence of one or more detersive, or "cleaning" surfactants.

Preferred methods for using the inventive compositions include washing the individuals hair with the compositions followed by rinsing with tap water, i.e., water having a hardness of at least about 60 ppm. Preferred pH values for conditioning shampoos according to the invention are from about 5–8, and more preferably from about 6–7.

Detersive Surfactant

The cleaning and conditioning formulations of the present invention typically comprise a detersive surfactant to provide cleaning performance to the composition.

The detersive surfactant, will generally be from about 5% to about 50%, preferably from about 8% to about 30%, more preferably from about 10% to about 25%, of the composition. A wide variety of surfactant materials may be utilized including anionic, nonionic, cationic, zwitterionic and amphoteric surfactants. Cationic detersive surfactants, if used, should not significantly interfere with the effectiveness of anionic surfactants included for detersive purposes.

Synthetic anionic detergents useful herein include alkyl and alkyl ether sulfates. These materials have the respective formulas $ROSO_3M$ and $RO(C_2H_4O)xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having from about 8 to about 24 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and/or ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree fo ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds, from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic surfactants are the water-soluble salts of the organic, sulfuric acid reaction products of the general formula:

R$_1$—SO$_3$—M wherein R$_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-,. ineso- and n-paraffins, having about 8 to about 24 carbon atoms, preferably about 12 to about 18 carbon atoms and a sulfonating agent, e.g., SO$_3$, H$_2$SO$_4$, oleum, obtained according to known sulfonation methods, including bleaching and hydrolysis. Preferred are alkali metal and ammonium sulfonated C$_{12-18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants fo this variety are set forth in U.S. Pat. Nos. 2,486,921; 2,486,922; and 2,396,278.

Still other anionic synthetic surfactants include the class designed as succinamates. This class includes such surface active agents as disodium N-octadecylsulfosuccinamate; tetrasodium N-(1,2-dicarboxyethyl)-N-octadecylsulfosuccinamate; diamul ester cinic acid; dioctyl esters of sodium sulfosuccinic acid.

Other suitable anionic surfactants utilizable herein are olefin sulfonates having about 12 to about 24 carbon atoms. the term "olefin sulfonates" is used herein to mean compounds which can be produced by the sulfonation of α-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid SO$_2$, chlorinated hydrocarbons, etc., when used in the liquid form, or by air, nitrogen, gaseous SO$_2$, etc., when used in the gaseous form.

The α-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecone; 1=tetradecene; 1-hexadecone; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions. proportion of reactants, the nature of the starting olefins and impurities in the olefin stock and side reactions during the sulfonation process.

A specific α-olefin sulfonate mixture of the above type is described more fully in the U.S. Pat. No. 3,332,880, Pflaumer and Kessler, issued Jul. 25, 1967, incorporated herein by reference.

Another class of anionic organic surfactants are the β-alkyloxy alkene sulfonates. These compounds have the following formula:

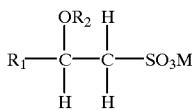

where R$_1$ is a straight chain alkyl group having from about 6 to about 20 carbon atoms, R$_2$ is a lower alkyl group having from about 1 (preferred) to about 3 carbon atoms, and M is a water-soluble cation as hereinbefore described.

Specific examples of β-alkoxy-alkane-1- sulfonates, or alternatively 2-alkoxy-alkane-1-sulfonates, having low hardness (calcium ion) sensitivity useful herein include: potassium-β-methoxydecanesulfonate, sodium 2-methoxy-tridecanesulfonate, potassium 2-ethoxytetradecylsulfonate, sodium 2-isopropoxyhexadecylsulfonate, lithium 2-t-butoxytetradecyl-sulfonate, sodium β-methoxyoctacdecylsulfonate, and ammonium β-n-propoxydodecyl-sulfonate.

Alpha sulfonated methyl esters of fatty acids having 8–22 carbon atoms and their corresponding acid salts, e.g., sodium, potassium, ammonium, and triethanolammonium salts, may also be used as the detersive surfactant in the inventive compositions.

Many additional synthetic anionic surfactants are describe in *McCutcheon's, Emulsifiers and detergents,* 1993 *Annual,* published by M. C. Publishing Co., which is incorporated herein by reference. Also U.S. Pat. No. 3,929,678, Laughlin et al., issued Dec. 30, 1975, disclosed many other anionic as well as other surfactant type sand is incorporated herein by reference.

In addition, the inventive compositions may include sulfosuccinates and their corresponding acid addition salts and sulfoactates and their acid addition salts.

Nonionic surfactants, which can be used, preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to about 20 carbon atoms, preferably from about 6 to about 12, in either a straight chain or branched chain configuration, with ethylene oxide, the said ehtylene oxide being present in amounts equal fo from about 10 to about 60 moles of ethylene oxide per mole of alkyl phenol. The alkyl substituent in such compounds may be derived from polymerized propylene, diisobutylene, octane, or nonane, for example.

2. Those derived form the condensation of ethylene oxide with the product resulting form the reaction of propylene oxide and theylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensat having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1R_2R_3N \rightarrow 0$$

wherein $R_1$ contains an alkyl, alkenyl or monohydroxy alkyl radical fo from about 8 to about 18 carbon atoms, from 0 to about 10 ethylene oxide moieties, and from 0 to abut 1 glycerol moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide , dimethyldecylamine oxide, dimethyl-tetradecylamine oxide, 3,6,9-trioxaheptadecyldiethylamine oxide, de(2-hydroxyethyl)-tetradecylamine oxide, 2-dodecoxyethyldimethylamine oxide, 3-dodecoxy-2-hydroxypropyl di(3-hydroxypropyl) amine oxide, dimethylhexadecylamine oxide.

5. Long chain tertiary phosphine oxide corresponding to the following general formula:

$$RR'R''P \rightarrow 0$$

wherein R contains an alkyl, alkenyl or monohydroxyalkyl radical ranging from about 8 to about 18 carbon atoms in chain length, from 0 to about 10 ethylene oxide moieties and from 0 to about 1 glycerol moiety and R' and R'' are each alkyl or monohydroxyalkyl groups containing from a bout 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyl di(2-hydroxyethyl) phosphine oxide, stearyldimethylphosphine oxide, cetylethylpropylphosphine oxide, oleyldiethylphosphine oxide, dodecyl-diethylp[hosphine oxide, tetradecyldiethyl-phosphine oxide, dodecyldipropylphosphine oxide dodecyl- di(hydroxymethyl phosphine oxide, dodecyldi(2- hydroxyethyl) phosphine oxide, tetradecylmethyl-2-hydroxypropylphosphine oxide, oleydimethylphosphin oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glycerol moiety. Examples include: octadecyl methyl sulfoxide, 2-ketotridecyl methyl sulfoxide, 3,6,9-trixaoctadecyl 2-hydroxyethyl sulfoxide, dodecyl methyl sulfoxide, oleyl 3-hydroxypropyl sulfoxide, tetradecyl methyl sulfoxide, 3-methoxytridedecyl methyl sulfoxide, 3-hydroxytridecyl methyl sulfoxide, 3- hydroxy-4-dodecoxybutyl methyl sulfoxide.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from abut 8 to about 18 carbon atoms and one contains an anionic group, e.g., carboxy, sulfonate, sulfate, phosphate, or phosphonate. A general formula for these compounds is:

$$R^2 - \underset{\underset{(R^3)_x}{|}}{Y^{(+)}} - CH_2 - R^4 Z^{(-)}$$

wherein $R^2$ contains an alkyl, alkenyl, or hydroxy alkyl radical of from about 8 to about 18 carbon atoms, from 0 to about 10 ethylene oxide moieties and from 0 to abut 1 glycerol moiety; Y is selected from the group consisting of nitrogen, phosphorus, and sulfur atoms, $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

EXAMPLES OF SUCH SURFACTANTS INCLUDE:

4-[N,N-di(2-hydroxyethyl)-N-octadecyammonio]-butane-1-carboxylate;

5-[S-3-hydroxypropl-S-hexadecylsulfonio]-3-hydroxypentane-1-sulfate;

3-[P,P-diethyl-P-3, 6, 0-trioxatetradexocylphosphonio]-2-hydroxy-propane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonia)-2-hydroxypropane-1-sulfonate;

4-[N,N-di(2-hydroxyethyl)-N-(2-hydroxydodecyl) ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines can also be useful in the present invention. Examples of betaines useful herein include the high alkyl betaines, such as coco dimethyl carboxymethyl betaine, cocoamidopropyl, betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-2-hydroxypropyl) carboxymethyl betaine, oleyl dimethyl gamma-carboxypropyl betaine, and lauryl bis-(2-hydroxypropyl)alpha-carboxymethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(Ch_2)_3$ radical is attached to the nitrogen atom of the betaine are also useful in this invention. Preferred betaines for use in the present compositions are cocoamidopropyl betaine, cocobetaine, alruyl amidopropyl betaine, and oleyl betaine.

Example of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains ana nionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Cationic detersive surfactants can also be used, although the use of anionic, nonionic, amphoteric, and zwitterionic surfactants is preferred. Cationic detersive surfactants are well known in the art. Generally, the cationic detersive surfactants will be quaternary ammonium compounds or amino compounds that are positively charge when dissolved in the compositions hereof as well as at neutral pH.

The above-mentioned surfactants can be used alone or in combination in the hair care compositions of the present invention. Preferred surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocyl sulfate, monoethanolamine lauryl sulfate, sodium tridecyl benzene sulfonate, sodium dodecyl benzene sulfonate, cocamidopropyl betaine, cocobetaine, lauryl amido propyl betaine, oleyl betaine, and cocoamphocarboxyglycinate.

The most preferred shampoos of the present invention contain specific combinations of surfactants. The preferred shampoos comprise from about 1–15% by weight of nonionic surfactant, 5–20% by weight of anionic surfactant, and 1.5% to about 10% of the sucroglyceride.

Optional Components

The compositions herein can contain a variety of non-essential optional components. Such optional ingredients include, for example, preservative such as benzyl alcohol, methyl paraben, propyl paraben and imidazolidinyl urea; cationic conditioning agents, including both cationic conditioning surfactants and cationic conditioning polymers; thickeners and viscosity modifiers such as a diethanolamide of a long chain fatty acid (e.g., PEG 3lauramide), block polymers of ethylene oxide and propylene oxide such as Pluronic F88 offered by BASF Wyandotte, sodium chloride, sodium sulfate, ammonium zylene sulfonate, ethyl alcohol, and polyhydric alcohols such as, for example, propylene glycol and polyvinyl alcohol; gelling agents such as hydroxyethyl cellulose; pH adjusting agents such as citric acid, succinic acid, phosphoric acid, sodium hydroxide, sodium carbonate, etc.; perfumes; dyes; and sequestering agents such as disodium ethylenediamine tetraacetate. This list of optional ingredients is not meant to be exclusive, and other optional components can be utilized.

These optional ingredients generally are used individually at a level of from about 0.01% to about 10%, most commonly from about 0.5% to abut 5.0% by weight of the composition.

The inventive compositions may optionally contain a nonvolatile, nonionic silicone conditioning agent. The silicone conditioning agent for use herein in shampoo compositions will preferably have viscosity fo from abut 1,000 to about 2,000,000 centistokes at 25° C., more preferably from about 10,000 to about 1,800,000 centistokes, even more preferably from about 100,000 to about 1,500,000 centistokes. Lower viscosity nonvolatile silicone fluids, however, can also be used and may be desirable particularly in the case of hair rinse compositions. Volatile silicone fluids, typically have viscosity less than 5 centistokes at 25° C., may also be utilized in hair rinse compositions. The leven of volatile silicones in shampoo compositions, however, is preferably at levels of less than about 0.5% by weight of the total composition. The viscosity can be measured by means of a glass capillary viscometer as set forth in Dow Corning Corporate Test Method CTM0004, Jul. 20, 1970.

Suitable nonvolatile silicone fluids for use in hair conditioning agents include polyalkyl siloxanes, polyaryl siloxanes, polyalkylaryl siloxanes, polyether siloxane copolymer and mixtures thereof. However, any silicone fluid having hair conditioning properties may be used. As used hereinafter, the term "insoluble " in reference to silicone fluid mean that the silicone material in not soluble in either water or in the hair conditioning composition. The term "nonvolatile" in reference to the silicone fluid as used herein shall be interpretered according to the meaning well understood to those skilled in the art, i.e., the silicone fluid exhibits very low or no significant vapor pressure at ambient conditions. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000 centistokes. The term "silicone", as used herein, shall be synonymous with the term "polysiloxane".

The nonvolatile polyalkyl siloxane fluids that may be used include, for example, polydimethylsloxanes. These siloxanes are available, for example, from the General Electric Company as SF 1075 methyl phenyl fluid or from Dow Corning as 556 Cosmetic Grade Fluid.

The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the following structure:

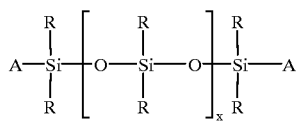

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Green; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is Silicon Compounds distributed by Petrarch Systems. Inc. 1984. this reference provides an extensive (though not exclusive) listing of suitable silicone fluids.

In certain embodiments, the hair conditioning compositions optionally may include a suspending agent for the optional silicone hair conditioning component.

The suspending agents useful in the present compositions include any of several long chain acyl derivative materials or mixtures of such materials, such as long chain acyl derivatives, long chain amine oxides, and mixtures thereof, wherein such suspending agents are present in the composition in crystalline form. These suspending agents are described in U.S. Pat. No. 4,741,855, Grote and Russell, issued May 3, 1988, incorporated herein by reference. Included are ethylene glycol esters of fatty acids having from about 16 to about 22 carbon atoms. Preferred are the ethylene glycol stearates, both mono and disterate, but particularly the disterate containing less than about 7% of the mono stearate. Other suspending agents found useful are alkanol atoms, preferably about 16 to 18 carbon atoms. Preferred alkanol amides are stearic monethanolamide, stearic diethanolamide, stearic monisopropanolamide and stearic monethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide DEA disterate, stearamide MEA stearate).

Still other suitable suspending agents are alkyl ($C_{18}$–$C_{22}$) dimethyl amine oxides such as stearyl dimethyl amine oxide. If the compositions contain an amine oxide or a long chain acyl derivative as a surfactant the suspending function could also be provided by such surfactant and additional suspending agent may not be needed if the level of those materials are at least the minimum level given below.

Other long chain acyl derivatives that can be used include N,N-dihydroxycarbyl amido benzoic acid and soluble salts thereof (e.g., Na and K salts), particularly N,N-di (hydrogenated $C_{16}$, $C_{18}$ and tallow amido benzoic acid species of this family, which are commercially available from Stepan Company (Northfield, Ill., USA).

The long chain acyl derivative materials, when utilized as the suspending agent, are typically present in pourable, liquid formulations at a level of from about 0.1% to about 5.0% preferably from about 0.5% to about 3.0%. The suspending agent serves to assist in suspending the silicone material and may give pearlescence to the product. Mixtures of suspending agents are also suitable for use in the compositions of this invention.

Another type of suspending agent that can be used is xanthan gum. Shampoo compositions utilizing xanthan gum as a suspending agent for the silicone hair conditioning component are described in U.S. Pat. No. 4,788,006, Bolich and Williams, issued Nov. 29, 1988, incorporated herein by reference. Xanthan gum is biosynthetic gum material that is commercially available. It is a heteropolysaccharide with a molecular weight of greater than 1 million. It is believed to contain D-glucose, D-mammose and D-glucuronate in the molar ratio of 2:8:2.0:2.0. The polysaccharide is partially acetylated with 4.7% acetyl. This information and other is found in Whistler, Roy L. Editor *Industrial Gums—Polysaccharides and Their Derivatives* New York: Academic Press, 1973. Kelco, A division of Merck & Co., Inc. offers xanthan gum as Keltrol®. The gum, when used as the silicone hair conditioning component suspending agent, will typically be present in pourable, liquid formulations at a level of from about 0.3% to about 3%, preferably from about 0.4% to about 1.2% in the compositions of the present invention.

Combinations of long chain acyl derivatives and xanthan gum are disclosed as a suspending agent for silicone hair conditioners in U.S. Pat. No. 4,704,272, Oh et al., issued Nov. 3, 1987, incorporated herein by reference, and may also be used in the present compositions. Gel formulations have high levels of suspending agent relative to pourable, liquid formulations when used as the primary means of imparting the gel-like viscosity to the composition. In such compositions, the suspending agent will typically be present at levels of from about 0.1 to about 5%. Alternately, other materials can be used to impart a gel-like viscosity to the composition, such as gelling agents (e.g., hydroxyethyl cellulose), thickeners, viscosity modifiers, etc. Mixtures of these materials can also be used.

A variety of cationic surfactants useful as detersive surfactants and as conditioning agents are well known in the art. These materials contain amino or quaternary ammonium hydrophilic moieties which are positively charged when dissolved in the aqueous composition of the present invention. Whether the cationic surfactant functions as a detersive surfactant or a conditioning agent, or both, will depend upon the particular compound as is well understood by those skilled in the art. In general, compounds with longer chain length moieties attached to the cationic nitgogen tend to exhibit greater conditioning benefits. Cationic surfactants among those useful herein are disclosed in the following documents, all incorporated by reference herein: M. C. Publishing Co., *McCutcheon's, Detergents & Emulsifiers,* (North American edition 1993); Schwartz et al., *Surface Active Agents, Their Chemistry and Technology,* New York; Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Quaternary ammonium salts include dialkldimethylammonium chlorides and trialkyl methyl ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). These types of cationic surfactants are useful as hair conditioning agents. Examples of quaternary ammonium salts useful herein include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyol ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride and tricetyl methyl ammonium chloride are particularly preferred quaternary ammonium salts. Preferred of the conventional cationic conditioning agents are cetyl tirmethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; these materials may also provide anti-static benefits to the present shampoo compositions.

Salts of primary, secondary and tertiary fatty amines are also suitable cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine ethyl stearlamine, N-tallowpropane diamine, ethoxylated (5 moles E.O.) stearylamine, dihydroxy ethyl stearylamine, and arachidyl-behenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Cationic conditioning surfactants especially useful in shampoo formulations are quaternary ammonium or amino compounds having at least one N-radical containing one or more nonionic hydrophilic moieties selected from alkoxy, polyoxyalkylene, alkylamido, hydroxyalkyl, and alkylester moieties, and combinations thereof. The surfactant contains at least one hydrophilic omiety within 4, preferably within 3, carbon atoms (inclusive) of the quaternary nitrogen or cationic amino nitrogen. Additionally, carbon atoms that are part of a hydrophilic moiety, e.g., carbon atoms carbon atoms in a hydrophilic polyoxyalkylene (e.g., —CH$_2$—CH$_2$—O—), that are adjacent to other hydrophilic moieties are not counted when determining the number of hydrophilic moieties within 4, or preferably 3, carbon atoms of the cationic nitrogen. In general, the alkyl portion of any hydrophilic moiety is preferably a C$_1$–C$_3$ alkyl. Suitable hydrophile-conbtaining radicals include, for example, thoxy, propoxy, polyoxyethylene, polyoxypropylene, ethylamido, propylamido, hydroxymethyl, hydroxyethyl, hydroxypropyl, methylester, ethylester, propylester, or mixtures thereof, as nonionic hydrophile moieties. The amino surfactants must be positively charged at the pH of the shampoo compositions. Generally, the pH of the shampoo compositions will be less than about 10, typically from about 3 to about 9.

Among the quaternary ammonium cationic surfactants useful herein are those of the general formula

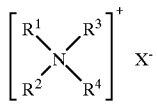

wherein R$_1$, R$_2$, R$_3$ and R$_4$ radicals comprise, independently, substituted or unsubstituted hydrocarbyl chains of from 1 to about 30 carbon atoms, or a hydrocarbyl having from 1 to about 30 carbon atoms and containing one or more aromatic, ether, ester, amido, or amino moieties present as substituents or as linkages in the radical chain, wherein at least one of the R$_1$–R$_4$ radicals contains one or more hydrophilic moieties selected from alkoxy (preferably C$_1$–C$_3$ alkoxy), polyoxyalkylene (preferably C$_1$–C$_3$ polyoxyalkylene), alkylamido, hydroxyalkyl, alkylester, and combinations thereof. Preferably, the cationic conditioning surfactant contains from 2 to about 10 nonionic hydrophile moieties located within the above stated ranges. For purposes herein, each hydrophilic amido, alkoxy, hydroxyalkyl, alkylester, alkylamido or other unit is considered to be a distinct nonionic hydrophile moiety. X is a soluble salt forming anion preferably selected from halogen (especially chlorine), acetate, phosphate, nitrate, sulfonate, and alkyl sulfate radicals.

Preferred quaternary ammonium salts include polyoxyethylene (2) stearyl methyl ammonium chloride, methyl bis (hydrogenated tallowamidoethyl) 2-hydroxyethyl ammonium methyl sulfate, polyoxypropylene (9) diethyl methyl ammonium chloride, tripolyoxyethylene (total PEG-10) stearyl ammonium phosphate, bis(N-hydroxyethyl -2-oleyl imidazolinium chloride) polyethylene glycol (1), and isododecylbenzyl triethanolammonium chloride.

Other ammonium quaternary and amino surfactants include those of the above general formula in the form of ring structures formed by covalently linking two of the radicals. Examples of such cationic surfactants include imidazolines, imidazoliniums, and pyridiniums, etc., wherein said surfactant has at least one nonionic hydrophile-containing radical as set forth above. Specific examples include 2-heptadecyl-4,5-dihydro-1H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxoctadecyl)oxy]ethyl]amino]ethyl] pyridinium chloride.

Salts of primary, secondary and tertiary fatty amines are also preferred cationic surfactant materials. The alkyl groups of such amines preferably have from about 1 to about 30 carbon atoms and must contain at least one, preferably 2 to about 10, nonionic hydrophilic moieties selected from alkoxy, polyoxyalkylene, alkylamido, hydroxyalkyl, and alkylester moieties, and mixtures thereof. Secondary and tertiary amines are preferred, tertiary amines are particularly preferred. Specific examples of suitable amines include diethyl aminoethyl polyoxyethylene (5) laurate, coco-polyglyceryl-4 hydroxypropyl dihydroxy ethylamine, and dihydroxyethyl tallowamine hydrochloride.

The pH of the present compositions is not generally critical and may be in the range of from 2 to about 10, preferably from about 3 to about 9, more preferably from about 4 to about 8.

Method of Manufacture

The compositions of the invention may be prepared by various methods, two of which are described below for exemplification only.

Method 1

The compositions of the present invention, in general, can be made by mixing the base components, e.g., water, the surfactants, and the sucroglyceride conditioning agent at elevated temperature, e.g., about 170–180° F. for about 20–25 minutes. The mixture is emulsified and subsequently cooled to room temperature.

Method 2

Alternatively, water and the surfactants may be first combined and heated to about 170–180° F. To the resulting heated surfactant mixture is then added a secondary mixture of sucroglyceride, glycerol and any optional water-insoluble components. Where the secondary mixture has been pre-heated to about 170–180° F. The water-insoluble components may comprise glycerin and any optional conditioning or sunscreen agents, or vitamins. After the mixture of sucroglyceride and water-insoluble components is added to the surfactant mixture, the composition is emulsified for about 20–25 minutes and subsequently cooled to room temperature. Optionally, preservative may be added to the mixture at about 100° F., and the pH and viscosity may be adjusted as necessary with, for example, sodium hydroxide, ammonium hydroxide, or citric acid.

Method of Use

The shampoo compositions of the invention are used in a conventional manner for cleaning hair. An effective amount of the composition for cleaning and conditioning hair, typically, from about 1 g to about 20 g of the composition, preferably about 3–5 ml, is applied to wet hair. Application to the hair typically includes working the composition through the hair to create a lather such that most or all of the hair is contacted with the lather. The lather may be retained on the hair for a short time before rinsing, e.g., from about 1 to 4 minutes, or may be immediately rinsed from the hair. This washing procedure may be repeated as necessary.

Subsequent to washing with the inventive compositions, the hair is found to be clean, manageable and easy to comb and style, without the need for an additional conditioning step.

All documents, e.g., patents and journal articles, cited above or below are hereby incorporated by reference in their entirety.

One skilled in the art will recognize that modifications may be made in the present invention without deviating from the spirit or scope of the invention. The invention is illustrated further by the following examples which are not to be construed as limiting the invention or scope of the specific procedures described herein.

In the following examples, all percentages are expressed in percent by weight or percent by weight of active material, unless otherwise noted.

In each of the following examples where a formulation is evaluated, the water used to wash the hair or skin or other substrate is ordinary tap water of moderate hardness.

EXAMPLE 1

Preparation of Sucroglyceride Derived from Tallow Fatty Acid Triglyceride and Sucrose A 1.5 L jacketed resin kettle, equipped with a 5-blade mechanical stirrer and a thermocouple was charged with melted hardened tallow (125 g). While stirring, $K_2CO_3$ (13.8 g) and sucrose (53.1 g) were added and the mixture stirred intensely at 123° C.±1° C.

After 10 hours, mixing was stopped and the product was allowed to cool and solidify, resulting in 190 g of a beige solid. The resulting product had the following composition:

| Component | Weight % |
|---|---|
| Total Glycerine Soap | 1.93 |
| C8[1] | 0.00 |
| C10 | 0.00 |
| C12 | 0.00 |
| C14 | 0.79 |
| C15 | 0.16 |
| C16 | 7.92 |
| C17 | 0.30 |
| C18 | 20.22 |
| C20 | 0.60 |
| C22 | 0.36 |
| Total soap | 30.35 |
| Monoglycerides | |
| C8 | 0.00 |
| C10 | 0.00 |
| C12 | 0.00 |
| C14 | 0.32 |
| C15 | 0.06 |
| C16 | 3.17 |
| C17 | 0.12 |
| C18 | 8.10 |
| C20 | 0.24 |
| C22 | 0.36 |
| Total Monoglycerides | 12.16 |
| Total Sucrose | 9.97 |
| Sucrose Mono Esters | |
| C8 | 0.00 |
| C10 | 0.00 |
| C12 | 0.00 |
| C14 | 0.76 |
| C15 | 0.14 |
| C16 | 7.65 |
| C17 | 0.29 |
| C18 | 19.51 |
| C20 | 0.59 |
| C14 | 0.36 |
| Total Sucrose Mono Esters | 29.30 |
| Total Di- and Triglycerides: | 16.29 |

[1]chain length of fatty acids from glyceride

EXAMPLE 2

Preparation of Sucroglyceride Derived from Hydrogenated Vegetable Oil and Sucrose Wecobee M (hydrogenated vegetable oil, 80 g), sucrose (34 g), $K_2CO_3$ (8 g), and a heel of previously prepared product (6.5 g) were combined as described above to afford 110 g of a light creamy solid containing 21% sucrose monoester.

This product had the following compositions:

| Component | Weight % |
|---|---|
| Total Glycerine Soap | 1.78 |
| C8 | 0.78 |

-continued

| Component | Weight % |
|---|---|
| C10 | 0.72 |
| C12 | 10.96 |
| C14 | 3.86 |
| C16 | 2.12 |
| C18 | 5.31 |
| Total Soap Monoglycerides | 23.75 |
| C8 | 0.35 |
| C10 | 0.32 |
| C12 | 4.97 |
| C14 | 1.74 |
| C16 | 0.96 |
| C18 | 2.41 |
| Total Monoglycerides | 10.75 |
| Total Sucrose Sucrose Mono Esters | 10.02 |
| C8 | 0.71 |
| C10 | 0.66 |
| C12 | 9.86 |
| C14 | 3.48 |
| C16 | 1.90 |
| C18 | 4.78 |
| Total Sucrose Mono Esters | 21.39 |
| Total Di- and Triglycerides | 32.31 |

EXAMPLE 3

Preparation of Sucrose Glyceride Derived from Caprylic/Capric Triglycerides and Sucrose Neobee M-5 (Caprylic/Capric Triglycerides, 100 g), Sucrose (68.4 g) $K_2CO_3$ (14.5 g), and a heel (9.0 g) were combined as described above to afford 150 g of a yellow wax.

EXAMPLE 4

To a suitable vessel equipped with agitation, heating, and cooling means is added water and, while heating slowly, ammonium lauryl sulfate and coco diethanolamide. At about 170–180° F., a sucroglyceride component (prepared by transesterification of cottonseed oil and sucrose using the procedure described above to have the composition shown as Formulation F2 below) is added to the vessel and the resulting mixture emulsified for about 20–30 minutes at a moderate speed at a temperature of about 175–180° F. The mixture is then cooled to 100° F. at which point a preservative is optionally added. pH is measured and adjusted as necessary with sodium hydroxide or citric acid to about 6.5–6.8. The viscosity may be measured and adjusted to from about 4000–5000 cps with ammonium chloride.

The composition of the resulting conditioning shampoo (Formulation 1) is shown below:

| Formulation 1 | |
|---|---|
| Component | % By Weight of Active Material |
| water (deionized) | Q.S. to 100 |
| ammonium lauryl sulfate | 12.5 |
| coco diethanolamide | 2.0 |
| sucroglyceride | 4.0 |
| citric acid | Q.S. |
| sodium hydroxide (50% aqueous) | Q.S. |
| ammonium chloride | Q.S. |

Formulation 1 provides excellent detangling, wet combability, dry combability, static control, and shine as determined by evaluation on hair swatches and on human subjects having different hair profiles in a salon setting. This formulation also exhibited excellent long term stability at various storage temperatures and through three freeze-thaw cycles.

EXAMPLE 5

Formulation 2 is prepared according to Method 2 described above. The surfactant mixture is prepared to contain guar hydroxypropyl/trimonium chloride, ammonium lauryl sulfate, and coco diethanolamide. The secondary mixture contains glycerin, the sucroglyceride (product of transesterification of cottonseed oil and sucrose), mineral oil and octyl salicylate.

| Formulation 2 | |
|---|---|
| Ingredient | % By Weight of Active Material |
| water (deionized) | Q.S. to 100.0 |
| guar hydroxypropyl/trimonium chloride | 0.2 |
| ammonium lauryl sulfate | 12.5 |
| coco diethanolamide | 2.0 |
| glycerin | 5.0 |
| sucroglyceride | 3.5 |
| mineral oil | 0.5 |
| octyl salicylate | 0.2 |

EXAMPLE 6

A hair conditioner/rinse composition is prepared by adding to a suitable vessel water and heating the water to about 170–175° F. with agitation. A sucroglyceride component prepared by transesterification of cottonseed oil and sucrose to have the composition of formulation F2 below is then added to the vessel and dispersed. Cetyl alcohol is then added and the mixture emulsified for about 20–25 minutes at about 170–175° F. The mixture is then slowly cooled to about 90° F. at which point the pH is adjusted to about 5.0–5.5 with citric acid. The viscosity may be adjusted as needed.

The composition of the resulting conditioning conditioner/rinse formulation (Formulation 3) is shown below:

| Component | % By Weight |
|---|---|
| water (deionized) | Q.S. to 100.0 |
| sucroglyceride | 5.0 |
| Cetyl Alcohol | 1.5 |
| citric acid (50% aqueous) | Q.S. |

EXAMPLE 7

Conditioning/hair-relaxer/permanent formulations A and B are prepared by adding water to a suitable vessel, heating to about 170–175° F., and adding to the vessel a sucroglyceride prepared by transesterification of cottonseed oil and sucrose to have the composition of formulation F1 below. To this aqueous mixture is then slowly added a premixed and heated (170–175° F.) oil phase containing cetyl alcohol and glycerol stearate. The resulting mixture is then emulsified for about 20–25 minutes at 170–175° F., and cooled to about 90° F. At 90° F., 50% aqueous NaOH is added to Formulation A and sodium bisulfate is added to Formulation B.

The composition of the resulting formulations (Formulation A and B) are shown below:

|  | A<br>% By Weight | B<br>% By Weight |
|---|---|---|
| water (deionized) | Q.S. to 100.0 | Q.S. to 100.0 |
| Sucroglyceride | 2.0 | 2.0 |
| Glycerol monostearate | 1.0 | 1.0 |
| cetyl alcohol | 1.5 | 1.5 |
| NaOH (50% aqueous) | 4.0 | — |
| Sodium bisulfate | — | 2.0 |

EXAMPLE 8

The following compositions are prepared for addition to shampoo bases.

| Ingredient | F1 | F2 | F3 | F4 | F5 | F6 | F7 |
|---|---|---|---|---|---|---|---|
| Sucrose Ester | 18.0 | 7.0 | 14.5 | 13.0 | 100.0 | — | — |
| Sucrose | 10.0 | 14.5 | 1.8 | 1.3 | — | — | — |
| Soap | 35.0 | 30.0 | 15.5 | 27.0 | — | — | — |
| Monoglyceride | 11.0 | 30.0 | 10.0 | 9.0 | — | 100.0 | — |
| total of Di- and Triglycerides | 23.0 | 7.5 | 56.0 | 49.0 | — | — | — |
| Glycerin | <3 | 16.0 | 1.0 | 0.7 | — | — | 100.0 |

| Ingredient | F8 | F9 | F10 | F11 | F12 | F13 | F14 |
|---|---|---|---|---|---|---|---|
| Sucrose Ester | — | — | — | — | — | 10.0 | — |
| Sucrose | — | — | — | — | — | — | — |
| Soap | 100.0 | 33.3 | 50.0 | 50.0 | — | 36.0 | 33.3 |
| Monoglyceride | — | 33.3 | 50.0 | — | 50.0 | 36.0 | 33.3 |
| Total of Di- and Triglycerides | — | — | — | — | — | — | — |
| Glycerin | — | 33.3 | — | 50.0 | 50.0 | 18.0 | 33.3 |

| Ingredient | F15 | F16 | F17 | F18 | F19 | F20 | F21 | F22 |
|---|---|---|---|---|---|---|---|---|
| Sucrose Ester | 15.0 | 15.0 | 15.0 | 15.0 | 3.0 | 6.85 | 10.6 | 8.0 |
| Sucrose | 10.0 | 10.0 | 10.0 | 10.0 | 14.0 | 12.0 | 19.2 | — |
| Soap | 35.0 | 35.0 | 35.0 | 35.0 | 26.0 | 25.0 | 25.0 | 30.0 |
| Monoglyceride | 9.5 | 9.5 | 9.5 | 9.5 | 3.0 | 23.0 | 33.2 | 15.0 |
| Total of Di- and Triglycerides | 2.85 | 2.85 | 2.85 | 2.85 | 53.0 | 17.7 | 35.0 | 15.0 |
| Glycerin | 2.0 | 2.0 | 2.0 | 2.00 | <1.0 | 14.9 | 7.9 | 8.0 |

EXAMPLE 9

The above formulations F1–F22 were added to a shampoo base and evaluated for conditioning performance. The shampoo base contained the following components:

| Formulation 1 | |
|---|---|
| Component | weight % (active) |
| water (deionized) | Q.S. to 100 |
| ammonium lauryl sulfate | 12.5 |
| coco diethanolamide | 2.0 |
| citric acid | Q.S. |
| sodium hydroxide (50% aqueous) | Q.S. |
| ammonium chloride | Q.S. |

Each resulting shampoo formulation was evaluated in a salon setting on 10 human subjects. Their heads were washed with a shampoo prepared to contain one of formulations F1–22, the hair was then evaluated for wet combing and dry combing performance and rated on a scale of 0–4, where a rating of 4 indicates excellent conditioning and 0 indicates little conditioning of hair.

The salon performance data are presented below in Tables 1 and 2.

TABLE 1

| Formulation No. | Weight percent of formulation in shampoo | Wet Combing | Dry Combing |
|---|---|---|---|
| F1 | 5.0 | 3 | 3 |
| F2 | 5.0 | 3 | 3 |
| F3 | 5.0 | 1.3 | 2 |
| F4 | 5.0 | 3.6 | 3.7 |
| F5 | 5.0 | 1.2 | 1.5 |
| F6 | 5.0 | 1.2 | 1.5 |
| F7 | 5.0 | 1.2 | 1.5 |
| F8 | 5.0 | 1.5 | 1.5 |
| F9 | 5.0 | 1 | 1 |
| F10 | 5.0 | 1.5 | 1.5 |
| F11 | 5.0 | 0.5 | 1.5 |

TABLE 2

| Formulation No. | Weight percent of formulation in shampoo | Wet Combing | Dry Combing |
|---|---|---|---|
| F12 | 5.0 | 1.5 | 1.2 |
| F13 | 5.0 | 2.2 | 1.5 |
| F14 | 15.0 | 1 | 2.1 |
| F15 | 0.5 | 1.5 | 1.5 |
| F16 | 1.5 | 1.7 | 2 |
| F17 | 2.5 | 2 | 2 |
| F18 | 3.5 | 2.2 | 2.5 |
| F19 | 5.0 | 1.8 | 2.4 |
| F20 | 5.0 | 3 | 3 |

TABLE 2-continued

| Formulation No. | Weight percent of formulation in shampoo | Wet Combing | Dry Combing |
|---|---|---|---|
| F21 | 5.0 | 3.6 | 2.5 |
| F22 | 5.0 | 2.0 | 2.0 |

EXAMPLE 10

A bath gel composition is prepared essentially according to the procedure set forth above in Example 4. The bath gel has the following compostion.

| Component | % By Weight of Active Material |
|---|---|
| water (deionized) | Q.S. to 100.0 |
| Sodium lauryl sulfate | 7.5 |
| Sodium laureth sulfate | 6.0 |
| Lauryl monoethanolamide | 2.0 |
| Sucroglyceride derived from cottonseed oil and sucrose | 4.0 |
| CaCl$_2$ | 0.5 |

EXAMPLE 11

A liquid soap/facial cleanser formulation is prepared essentially according to the procedure set forth in Example 4.

| Ingredient | % by Weight of Active Material |
|---|---|
| water (deionized) | Q.S. to 100.0 |
| sodium lauryl sulfate | 10.0 |
| cocamidopropyl betaine | 2.5 |
| glycerin | 2.0 |
| sucroglyceride derived from cottonseed oil and sucrose | 3.5 |

The bath gel prepared in Example 11, and the liquid soap/facial cleanser prepared in Example 12 both provided an excellent feel on skin after the formulations were rinsed from the skin and the skin dried.

EXAMPLE 12

Liquid cleaning compositions are prepared by combining the following components with a suitable amount of water to prepare a formulation containing approximately 34% of surfactants by weight of the final formulation.

| Ingredient | % by Weight Formulation C | % by Weight Formulation D |
|---|---|---|
| ammonium lauryl sulfate (28% active by weight) | 6.0 | 6.0 |
| sodium salt of alpha-sulfonated methyl ester of mixture of acids having an average of 12– 14 carbon atoms | 19.0 | — |
| sodium salt of alpha-sulfonated methyl ester of mixture of acids having an average of 12 carbon atoms | — | 19.0 |
| lauric myristic monoethanolamide | 5.0 | 5.0 |
| cocoamidopropyl betaine | 4.0 | 4.0 |
| sucroglyceride[1] | 2.0 | 2.0 |
| ethanol | 2.0 | 2.0 |
| pH | 5.5 | 5.5 |
| appearance | clear | clear |

[1]The sucroglyceride is derived from a mixture of triglycerides comprising the following chain lengths: 2.4% C$_6$, 70.9% C$_8$, 26.0% C$_{10}$, and 0.7% C$_{12}$.

From the foregoing it will be appreciated that, although specific embodiments of the invention have been described herein for purposes of illustration, various modifications may be made without deviating from the spirit and scope of the invention.

What is claimed is:

1. A composition suitable for conditioning hair and skin comprising:
   a) from about 5–50% by weight of an anionic detersive surfactant mixture comprising:
      i) an alpha sulfonated alkyl ester of the formula

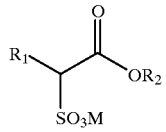

wherein R$_1$ is a C$_6$–C$_{32}$ hydrocarbyl or combination thereof, R$_2$ is a straight or branched chain C$_1$–C$_6$ hydrocarbyl or combination thereof, and M is hydrogen or sodium, potassium, calcium, magnesium, monoethanolammonium, diethanolammonium, triethanolammonium, or a mixture thereof; and
      ii) a sulfonated fatty acid, or a salt thereof, of the formula

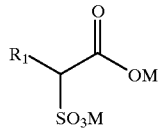

wherein R$_1$ is a C$_6$–C$_{32}$ hydrocarbyl or combination thereof, and each M is independently hydrogen, sodium, potassium, calcium, magnesium, monoethanolammonium, diethanolammonium, triethanolammonium, or a mixture thereof; and
   b) an effective conditioning amount of a sucroglyceride composition consisting of
      i) about 2–30% by weight of sucrose monoesters,
      ii) about 10–40% by weight of salts of aliphatic fatty acids having from 8 to 22 carbon atoms,
      iii) about 0–20% by weight of sucrose,
      iv) about 2–35% by weight monoglycerides, v) about 0.5–20% by weight of glycerin, and
vi) 2–55% by weight of a mixture consisting of diglycerides and triglycerides.

2. A composition according to claim 1, where the composition comprises about 0.5 to 15% by weight of the sucroglyceride composition.

3. A composition according to claim 1, where the composition comprises about 3 to 7% by weight of the sucroglyceride composition.

4. A composition according to claim 1, where the composition has a pH of about 5.0 to 8.0.

5. A composition according to claim 1, wherein the sucroglyceride composition is derived from sucrose and a triglyceride selected from the group consisting of caprylic/capric triglycerides, hydrogenated vegetable oil, cottonseed oil, and tallow.

6. A composition according to claim 1, wherein the composition comprises an emulsion of oil and water.

7. A composition according to claim 6, where the composition comprises about 0.5 to 15% by weight of the sucroglyceride composition.

8. A composition according to claim 6, where the composition comprises about 3 to 7% by weight of the sucroglyceride composition.

9. A composition according to claim 6, wherein the sucroglyceride composition is derived from sucrose and a triglyceride selected from the group consisting of caprylic/capric triglycerides, hydrogenated vegetable oil, cottonseed oil, and tallow.

10. A composition according to claim 1, wherein the anionic surfactant mixture further comprises an alkyl sulfate, an alkyl ether sulfate, an alkyl sulfosuccinamate, an alkyl sulfosuccinate, an alkyl isethionate, or an olefin sulfonate having about 12 to about 24 carbon atoms, or a mixture thereof.

11. A composition suitable for conditioning skin and hair comprising:
a) from about 18–28% by weight of an anionic detersive surfactant mixture comprising:
i) an alpha sulfonated alkyl ester of the formula

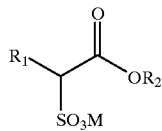

wherein $R_1$ is a $C_8$–$C_{16}$ hydrocarbyl or combination thereof, $R_2$ is a straight or branched chain $C_1$–$C_6$ hydrocarbyl or combination thereof, and M is hydrogen or sodium, potassium, calcium, magnesium, monoethanolammonium, diethanolammonium, triethanolammonium, or a mixture thereof; and
ii) a sulfonated fatty acid, or a salt thereof, of the formula

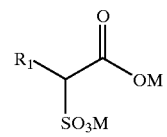

wherein $R_1$ is a $C_8$–$C_{16}$ hydrocarbyl or combination thereof, and each M is independently hydrogen, sodium, potassium, calcium, magnesium, monoethanolammonium, diethanolammonium, triethanolammonium, or a mixture thereof;
iii) an alkyl sulfate, an alkyl ether sulfate, an alkyl sulfosuccinamate, an alkyl sulfosuccinate, an alkyl isethionate, or an olefin sulfonate having about 10 to about 24 carbon atoms, or a mixture thereof,
b) about 1–3% by weight of a sucroglyceride composition consisting of
i) about 2–30% by weight of sucrose monoesters,
ii) about 10–40% by weight of salts of aliphatic fatty acids having from 8 to 22 carbon atoms
iii) about 0–20% by weight of sucrose,
iv) about 2–35% by weight monoglycerides,
v) about 0.5–20% by weight of glycerin, and
vi) 2–55% by weight of a mixture consisting of diglycerides and triglycerides,
c) about 3–8% by weight of a nonionic surfactant; and
d) about 2–6% by weight of a zwitterionic or amphoteric surfactant.

12. A composition according to claim 11, wherein the anionic detersive surfactant is present from about 23–27% by weight in the composition.

13. A composition according to claim 12, wherein the sucroglyceride composition is present from about 1.5–2.5% by weight in the composition.

14. A composition according to claim 13, wherein the nonionic surfactant is a fatty alkanolamide.

15. A composition according to claim 14, wherein the fatty alkanolamide is present from about 4–6% by weight in the composition.

16. A composition according to claim 13, wherein the zwitterionic surfactant is a betaine.

17. A composition according to claim 16, wherein the betaine is present from about 3–5% by weight in the composition.

18. A composition according to claim 14, wherein the fatty alkanolamide is lauric myristic monoethanolamine.

19. A composition according to claim 17, wherein the betaine is cocoamidopropyl betaine.

20. A composition according to claim 1, wherein each $R_1$ is independently $C_6$–$C_{22}$ alkyl and $R_2$ is methyl.

21. A composition according to claim 11, wherein each $R_1$ is independently $C_6$–$C_{22}$ alkyl and $R_2$ is methyl.

* * * * *

UNITED STATES PATENT AND TRADEMARK OFFICE
CERTIFICATE OF CORRECTION

PATENT NO. : 6,254,859 B1
DATED : July 3, 2001
INVENTOR(S) : Shapiro et al.

It is certified that error appears in the above-identified patent and that said Letters Patent is hereby corrected as shown below:

Title page,
Item [75], Inventors, please delete "Irene Shapiro, Buffalo Grove; Galina Tseitlina, Deerfield, both of IL (US)" and insert -- Irma Ryklin, Buffalo Grove, IL (US) --

Column 2,
Line 20, delete "noionic" and insert -- nonionic --;

Column 3,
Line 19, delete "fo" and insert -- of --;

Column 4,
Line 55, delete "fo" and insert -- of --;

Column 5,
Line 28, delete "fo" and insert -- of --;

Column 6,
Line 50, delete "ehtylene" and insert -- ethylene --;
Line 57, delete "theylene" and insert -- ethylene --;

Column 7,
Line 4, delete "condensat" and insert -- condensate --;
Line 46, delete "diethylp[hosphine" and insert -- diethylphosphine --;
Lines 50-51, delete "oleydimethylphosphin" and insert -- oleyldimethylphosphine --;

Column 8,
Line 65, delete "alruyl" and insert -- lauryl --;

Column 9,
Line 5, delete "ana nionic" and insert -- an anionic --;
Line 62, delete "polyhydric" and insert --polyhydridic --;

Column 10,
Line 17, delete "leven" and insert -- level --;
Line 32, delete "intepretered" and insert -- interpreted --;
Line 43, delete "polydimethylsloxanes" and insert -- polydimethylsiloxanes --;

Column 12,
Line 47, delete "nitgogen" and insert -- nitrogen --;
Line 59, delete "dialkldimethyl" and insert -- dialkyldimethyl --;

UNITED STATES PATENT AND TRADEMARK OFFICE
CERTIFICATE OF CORRECTION

PATENT NO. : 6,254,859 B1
DATED : July 3, 2001
INVENTOR(S) : Shapiro et al.

It is certified that error appears in the above-identified patent and that said Letters Patent is hereby corrected as shown below:

Column 13,
Line 19, delete "tirmethyl" and insert -- trimethyl --;
Line 52, delete "omeity" and insert -- moiety --;
Line 62, delete "conbtaining" and insert -- containing --;

Column 21,
Line 14, delete "compostion" and insert -- composition --.

Signed and Sealed this

Thirtieth Day of April, 2002

*Attest:*

*Attesting Officer*

JAMES E. ROGAN
*Director of the United States Patent and Trademark Office*